(12) United States Patent
Pan et al.

(10) Patent No.: US 12,336,754 B2
(45) Date of Patent: Jun. 24, 2025

(54) PORTABLE HAIR REMOVAL DEVICE

(71) Applicant: Shenzhen Ulike Smart Electronics Co., Ltd., Shenzhen (CN)

(72) Inventors: Yuping Pan, Shenzhen (CN); Shaoqing Fang, Shenzhen (CN)

(73) Assignee: SHENZHEN ULIKE SMART ELECTRONICS CO., LTD., Shenzhen (CN)

( * ) Notice: Subject to any disclaimer, the term of this patent is extended or adjusted under 35 U.S.C. 154(b) by 227 days.

(21) Appl. No.: 17/883,545

(22) Filed: Aug. 8, 2022

(65) Prior Publication Data

US 2022/0387103 A1  Dec. 8, 2022

Related U.S. Application Data

(63) Continuation of application No. PCT/CN2020/080842, filed on Mar. 24, 2020.

(30) Foreign Application Priority Data

Feb. 7, 2020 (CN) .......................... 202020157347.8

(51) Int. Cl.
*A61B 18/18* (2006.01)
*A61N 5/06* (2006.01)

(52) U.S. Cl.
CPC ............ *A61B 18/18* (2013.01); *A61N 5/0616* (2013.01); *A61B 2018/1807* (2013.01); *A61N 2005/0651* (2013.01); *A61N 2005/0663* (2013.01)

(58) Field of Classification Search
CPC ............ A61B 18/18; A61B 2018/1807; A61N 5/0616; A61N 2005/0651; A61N 2005/0663
USPC ............................................................ 606/9
See application file for complete search history.

(56) References Cited

U.S. PATENT DOCUMENTS

| | | | |
|---|---|---|---|
| 2005/0154382 A1 | 7/2005 | Altshuler et al. | |
| 2005/0177139 A1 | 8/2005 | Yamazaki et al. | |
| 2010/0069898 A1* | 3/2010 | O'Neil ................ | A61B 18/203 607/90 |

(Continued)

FOREIGN PATENT DOCUMENTS

| CN | 104799550 A | 7/2015 |
|---|---|---|
| CN | 105597236 A | 5/2016 |

(Continued)

OTHER PUBLICATIONS

European Search Report, European Application No. 20917492.9, mailed Jun. 4, 2023 (7 pages).

(Continued)

*Primary Examiner* — Aaron F Roane

(57) ABSTRACT

A portable hair removal device (10), comprising a head portion (30), and a housing (20) connected to one end of the head portion (30). An emitter capable of emitting light is provided in the housing (20), and the light emitted by the emitter passes through the head portion (30) and then acts on the skin for hair removal. The head portion (30) is provided with at least a phototherapy lamp (32), and light emitted by the phototherapy lamp (32) acts on the skin through the head (30) and takes care of the skin. The portable hair removal device (10) has rich functions and a good skin care effect.

20 Claims, 8 Drawing Sheets

(56) References Cited

U.S. PATENT DOCUMENTS

| | | | | |
|---|---|---|---|---|
| 2011/0307035 | A1* | 12/2011 | Tsao | A61N 5/0616 |
| | | | | 607/90 |
| 2018/0214712 | A1 | 8/2018 | Kim | |
| 2018/0344403 | A1 | 12/2018 | Gündogdu | |

FOREIGN PATENT DOCUMENTS

| | | | |
|---|---|---|---|
| CN | 106806995 | A | 6/2017 |
| CN | 207202931 | U | 4/2018 |
| CN | 109125938 | A | 1/2019 |
| CN | 209004194 | U | 6/2019 |
| CN | 209572304 | U | 11/2019 |
| EP | 0827716 | A2 | 3/1998 |
| JP | 2000316939 | A | 11/2000 |
| JP | 2006116088 | A | 5/2006 |
| JP | 2007020593 | A | 2/2007 |
| JP | 2015073744 | A | 4/2015 |
| JP | 2018033923 | A | 3/2018 |
| JP | 2019514517 | A | 6/2019 |
| JP | 2021506319 | A | 2/2021 |
| KR | 101403331 | B1 | 6/2014 |
| KR | 101426539 | B1 | 8/2014 |
| KR | 20170119185 | A | 10/2017 |
| KR | 20180099583 | A | 9/2018 |
| WO | 2015098427 | A1 | 7/2015 |
| WO | 2020035405 | A1 | 2/2020 |

OTHER PUBLICATIONS

Japanese Notice of Reasons for Refusal,Japanese Patent Application No. 2022-548250 ,mailed Jul. 25, 2023 (7 pages).
International search report and Written Opinion of the International Search Authority,International Application No. PCT/CN2020/080842,mailed Nov. 6, 2020 (11 pages).
Australian First Examination Report,Application No. 2020427144,mailed Oct. 12, 2023 (8 pages).
Australian Second Examination Report,Application No. 2020427144,mailed Nov. 29, 2023 (4 pages).
Canada Office Action,Canada Application No. 3,172,435, mailed Oct. 3, 2023 (4 pages).
Decision to Grant a Patent,Japanese Application No. 2022-548250, mailed Nov. 7, 2023 (6 pages).

* cited by examiner

PORTABLE HAIR REMOVAL DEVICE

CROSS REFERENCE TO RELATED APPLICATIONS

The present application is a continuation-application of International (PCT) Patent Application No. PCT/CN2020/080842, filed on Mar. 24, 2020, which claims foreign priority of the Chinese patent application No. 202020157347.8, filed on Feb. 7, 2020, and the entire contents of which are hereby incorporated by reference in their entireties.

TECHNICAL FIELD

The present disclosure relates to the field of electronic products, and in particular to portable hair removing device.

BACKGROUND

Optical hair removing is a non-invasive modern hair removing technique, which may safely, quickly and efficiently remove undesired body hair. In detail, optical hair removing may be performed based on selective photothermal principles, allowing light in specific wavelengths to penetrate the epidermis, without damaging hair follicles of the epidermis. Melanin in a hair shaft may selectively absorb light energy, the hair follicles may be heated and coagulated, and thus, may be necrosed. In this way, hair growth may be effectively slowed down, such that the hair may be removed.

However, as commonly known, the portable hair removing device in the art may only heat, coagulate and necrotize the hair follicles. Therefore, only one function may be achieved, the portable hair removing device in the art may not achieve further effect while acting on a skin surface. Therefore, a multi-functional portable hair removing device, which may achieve other functions in addition to removing hair, may be needed.

SUMMARY OF THE DISCLOSURE

In order to solve the defect that the portable hair removing device in the art can achieve only one function, the present disclosure provides a portable hair removing device.

According to an aspect of the present disclosure, a portable hair removing device is provided and includes. a head; a shell, connected to an end of the head; and an emitter, capable of emitting light and arranged inside the shell. The light emitted from the emitter is configured to pass through the head to act on skin to remove hair; the head is arranged with at least one phototherapeutic lamp; and light emitted from the at least one phototherapeutic lamp is configured to act on the skin through the head to provide cares for the skin.

According to another aspect of the present disclosure, a hair removing assembly is provided and includes: a head, configured to contact skin of a user and comprising a cold-compressing portion, a fixing portion, and a plurality of phototherapeutic lamps; and a connection portion, connected to the head and extending away from the skin of the user, wherein the connection portion comprises an emitter. A part of the cold-compressing portion extends through and is exposed from an end of the fixing portion away from the connection portion, and the plurality of phototherapeutic lamps are arranged to surround a periphery of the cold-compressing portion. The emitter is configured to emit light that is capable of passing through the cold-compressing portion to irradiate the skin, and each of the plurality of phototherapeutic lamps is configured emit light that is capable of irradiating the skin through the head.

According to still another aspect of the present disclosure, a portable hair removing device is provided an includes: a shell; a head, connected to the shell and configured to contact skin of a user, wherein the head and the shell cooperatively defines a receiving space, and the head comprises a cold-compressing portion, a fixing portion, and a plurality of phototherapeutic lamps; and a connection portion, received in the receiving space and connected to the head, wherein the connection portion comprises an emitter. A part of the cold-compressing portion is received in the receiving space and another part of the cold-compressing portion extends through and is exposed from an end of the fixing portion away from the connection portion, and the plurality of phototherapeutic lamps are arranged to surround a periphery of the cold-compressing portion. The emitter is configured to emit light that is capable of passing through the cold-compressing portion to irradiate the skin, and each of the plurality of phototherapeutic lamps is configured emit light that is capable of irradiating the skin through the head.

Figure 1:
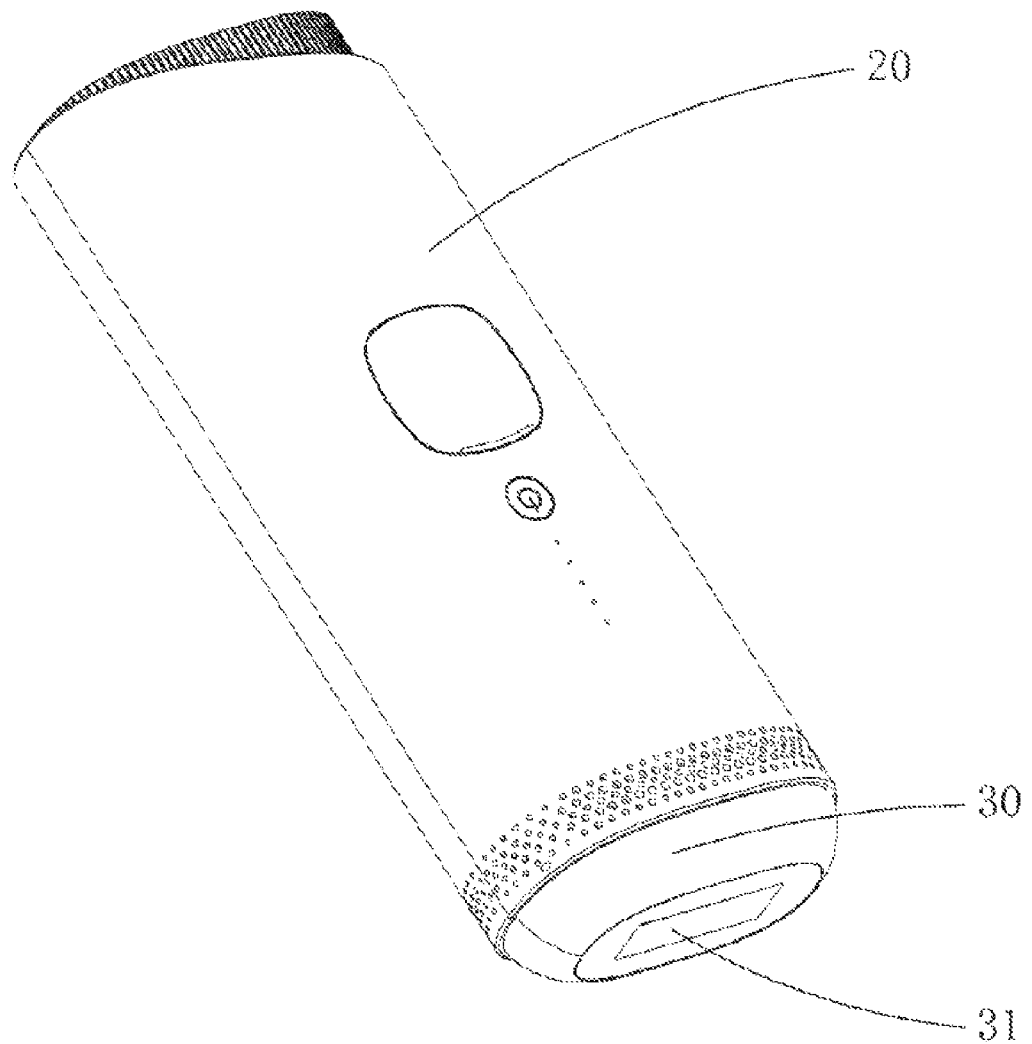
FIG. 1 is a perspective view of a portable hair removing device according to a first embodiment of the present disclosure.

REFERENCE NUMERALS IN THE DRAWINGS 10, portable hair removing device; 20, shell; 21, power switch; 22, control kay; 23, display lamp; 24, skin sensor lamp; 30, head; 31, cold-compressing portion; 32, phototherapeutic lamp; 33, PCB board; 331, through hole; 35, fixing portion; 40, connection portion; 41, emitter; 42, power supply assembly; 43, cooling assembly; 44, filter; 45, heat dissipation assembly; 46, capacitive touch sensor chip; 50, charging port; 90, portable hair removing device; 91, head; 92, shell; 93, emitter; 94, phototherapeutic lamp.

DETAILED DESCRIPTION

In order to illustrate objectives, technical solutions and advantages of the present disclosure more clearly, the present disclosure will be described in further detail below by referring to the accompanying drawings and embodiments.

It shall be understood that the specific embodiments described herein only explain the present disclosure and do not limit the present disclosure.

To be noted that, when an element is described as "being fixed to" another element, the element may be directly arranged on the another element or arranged inside the another element. When an element is described as "being connected to" another element, the element may be directly connected to the another element or may be arranged inside the another element. Terms "vertical", "horizontal", "left", "right" and similar expressions are used herein for illustrative purposes only.

Figure 2:
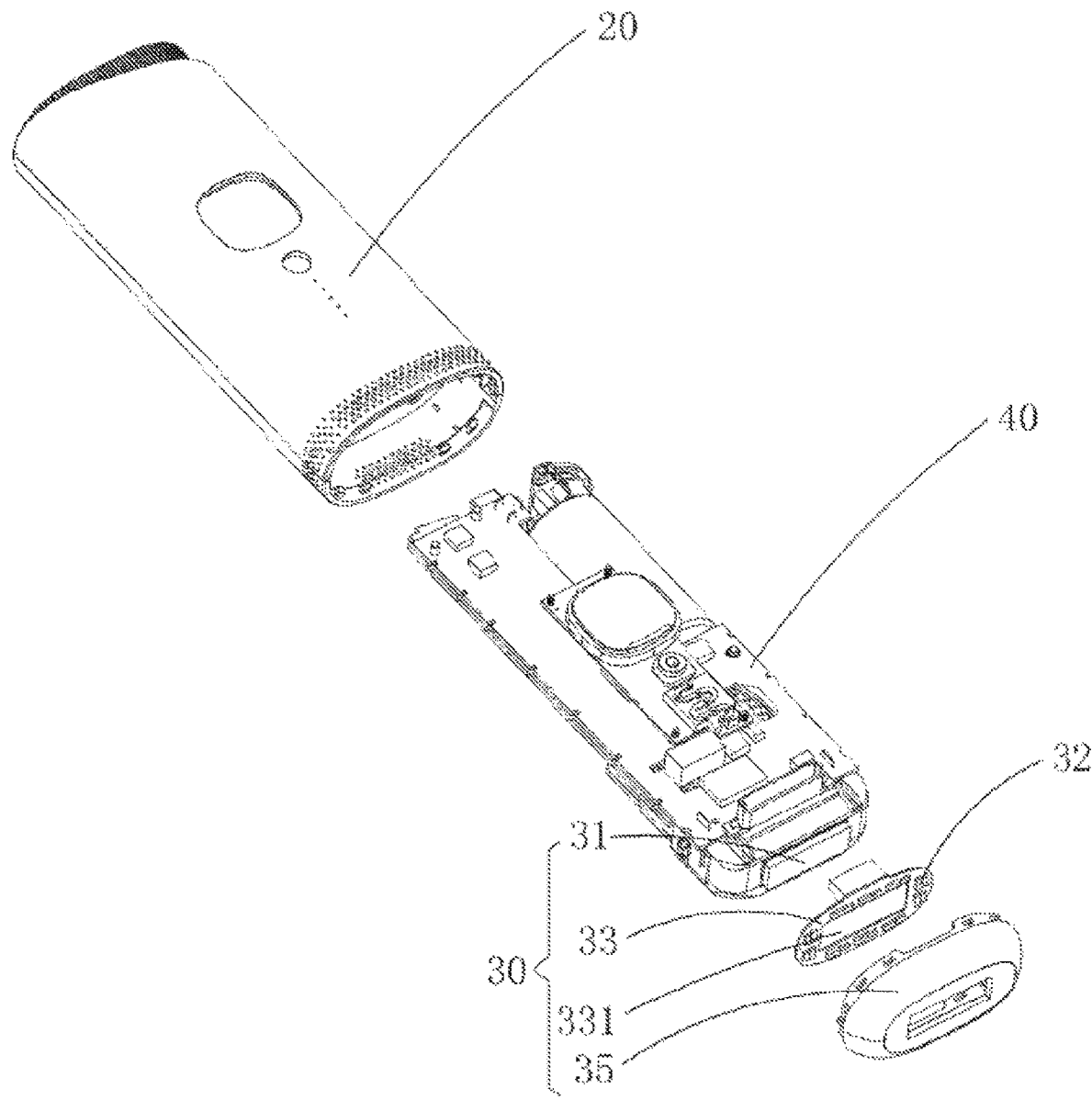
FIG. 2 is an explosive view of a portable hair removing device according to the first embodiment of the present disclosure.

As shown in FIG. 1 and FIG. 2, the first embodiment of the present disclosure provides a portable hair removing device 10. The portable hair removing device 10 may include a head 30, a shell 20 connected to an end of the head 30. The head 30 may further include a cold-compressing portion 31 and a fixing portion 35. The cold-compressing portion 31 may be partially received in the shell 20 and the fixing portion 35. An end of the fixing portion 35 away from the shell 20 may contact a skin surface of a user. The cold-compressing portion 31 may extend through and exposed from the end of the fixing portion 35 away from the shell 20. The cold-compressing portion 31 may directly contact a carrier of the skin. An emitter (not shown) may be arranged in the shell 20 and may emit light. The light emitted from the emitter may pass through the cold-compressing portion 31 and penetrate the skin surface to reach a root of a hair follicle, such that the hair follicle may be heated, coagulated, and necrosed, and therefore, the hair may be removed.

The shell 20 may be substantially configured to protect components inside the shell. An overall shape of the shell 20 may not be limited herein. The shell may be U-shaped, T-shaped, shuttle-shaped, strip-shaped, or stripped-cylindrical.

Further, the cold-compressing portion 31 may be made of crystal. In detail, the cold-compressing portion 31 may be made of sapphire, K9 glass, or crystal glass, as long as the crystal is light transmitting. In some embodiments, the cold-compressing portion 31 may be made of sapphire. The sapphire may cool the skin rapidly, such that damage to the skin may be reduced.

When performing optical hair removing on the skin, the cold-compressing portion 31 may contact surrounding of irradiated skin to cool the surrounding of the irradiated skin by cold-pressing the surrounding of the irradiated skin, such that burning pain of the irradiated skin may be reduced. In a process of optical hair removing, the cold-compressing portion 31 may produce a low temperature near 0 degrees, such that a skin area treated by the portable hair removing device may approach a freezing point. In this way, the burning pain of the skin may be reduced, and the cold-compressing portion 31 may not cause damage to the skin.

Figure 3:
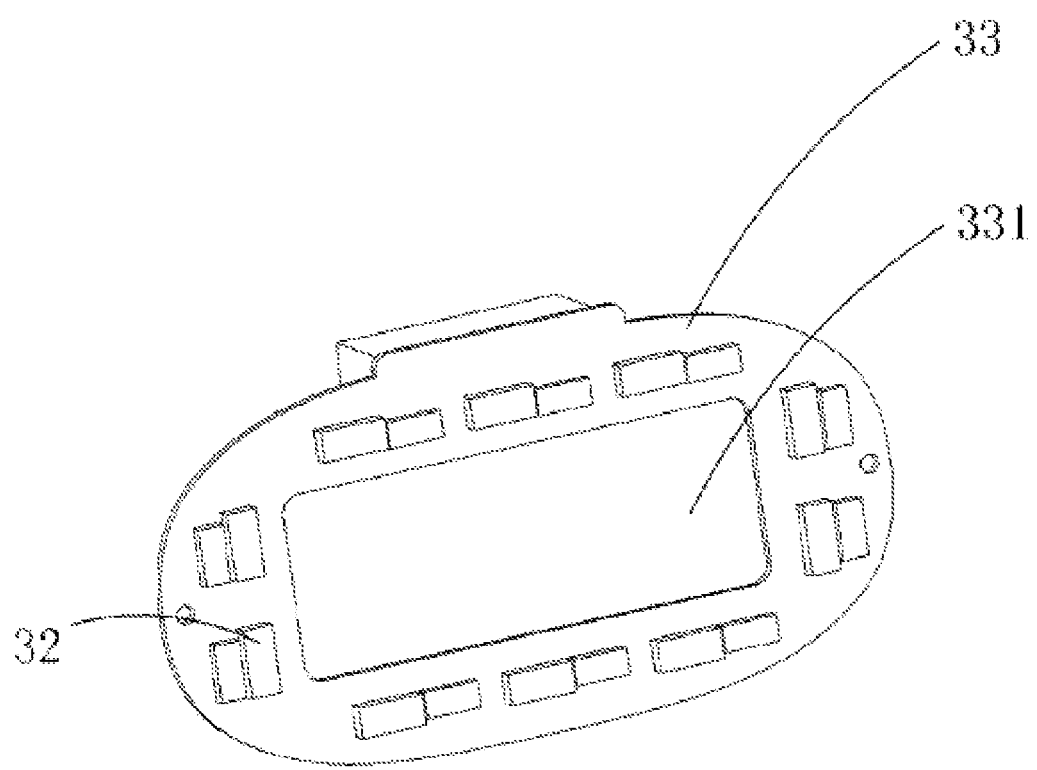
FIG. 3 is a perspective view of a PCB board of the portable hair removing device according to the first embodiment of the present disclosure.

As shown in FIG. 2 and FIG. 3, a center of the fixing portion 35 may define an opening. The cold-compressing portion 31 may extend through and fixedly received in the opening. The head 30 may further include a PCB board 33. The PCB board 33 may be disposed between the fixing portion 35 and the cold-compressing portion 31. The PCB board 33 may define a through hole 331 corresponding to the opening of the fixing portion 35. The cold-compressing portion 31 may extend through the through hole 331. The cold-compressing portion 31 may extend through the PCB board 33 and the fixing portion 35 successively. A side of the PCB board 33 facing the fixing portion 35 may be arranged with at least one phototherapeutic lamp 32. Phototherapeutic lamps 32 may be arranged into a ring shape and disposed to surround a periphery of the through hole 331. In some embodiments, the number of the at least one therapeutic lamp 32 is one, and the light therapeutic lamp 32 may be adjusted to emit light in various colors by a switch (not shown) arranged on the portable hair removing device 10. The phototherapeutic lamp 32 may emit red light, blue light, yellow light and a combination thereof. The at least one phototherapeutic lamp 32 may include at least one lamp emitting the red light, at least one lamp emitting the blue light, and at least one lamp emitting the yellow light. A plurality of phototherapeutic lamps that emit light in various colors are arranged alternately. Further, the light therapeutic lamp 32 may be an LED.

In some embodiments, the blue light emitted by the phototherapeutic lamp 32 may cause death of bacteria on the skin, inhibiting growth of the bacteria. Further, the blue light may improve sebum, having anti-inflammatory functions, reducing *acnes*, and reducing pores. In detail, wavelengths of the blue light may be in a range of 450 nm-490 nm. In detail, a wavelength of the blue light may be 450 nm, 460 nm, 467 nm, 480 nm, 485 nm or 490 nm. In some embodiments, the wavelength of the blue light may be 470 nm. The blue light having the wavelength in the above range may calm the skin and achieve anti-inflammatory, inhibiting bacterial growth.

The yellow light emitted by the phototherapeutic lamp 32 may brighten the skin and remove spots, providing better skin care effects. In detail, wavelengths of the yellow light may be in a range of 567 nm-607 nm. In detail, a wavelength of the yellow light may be 577 nm, 580 nm, 581 nm, 585 nm, 588 nm, 590 nm, 595 nm or 597 nm. In some embodiments, the wavelength of the yellow light may be 590 nm. The yellow light having the wavelength in the above range may improving a nutrient exchanging rate of cells and provide energy to the skin, reducing roughness of the skin.

The red light emitted by the phototherapeutic lamp 32 may improve activity of skin cells and promote metabolism of the skin cells. Further, the red light may reduce fine wrinkles, preventing skin from sagging and removing wrinkles. In detail, wavelengths of the red light may be in a range of 620 nm-660 nm. In detail, a wavelength of the red light may be 630 nm, 632 nm, 635 nm, 637 nm, 640 nm, 643 nm, 647 nm, or 650 nm. In some embodiments, the wavelength of the red light may be 630 nm. The red light having wavelengths in the above range may stimulate blood circulation of the skin, promote collagen growth and improve cell activity for renewal and growth.

According to the portable hair removing device 10 of the present disclosure, while the cold-compressing portion 31 is contacting the skin to remove hair, the phototherapeutic lamp 32 may further achieve skin care. Integrating the phototherapeutic lamp 32 with the cold-compressing portion 31 into one structure may combine skin care with hair removing, such that the portable hair removing device 10 may be multi-functional, improving the user's experience.

Figure 4:
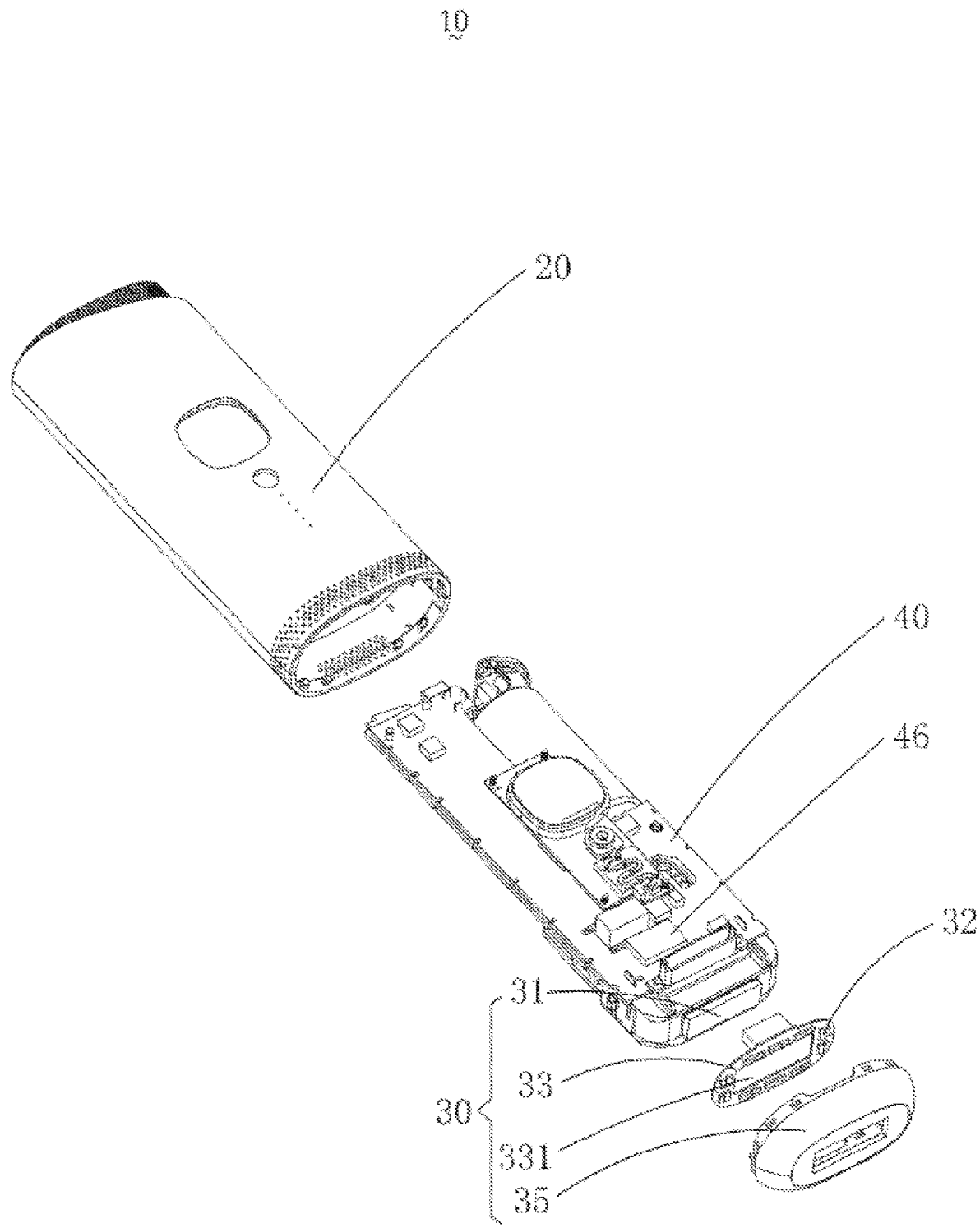
FIG. 4 is an explosive view of the portable hair removing device according to the first embodiment of the present disclosure.

As shown in FIG. 4, the capacitive touch sensor chip 46 may be arranged in the shell 20. A wire (not shown) may be arranged on the PCB board 33 and may be electrically connected to the capacitive touch sensor chip 46. Inductive capacitance may be generated between the wire and the skin. The capacitive touch sensor chip 46 may sense a change in a capacitance value between the wire and the skin to control the phototherapeutic lamp 32 to be turned on or off.

When the phototherapeutic lamp 32 is contacting or separating from the skin, the capacitance value between the wire and the skin may change. The capacitive touch sensing chip 46 may sense the change in the capacitance value to control the phototherapeutic lamp 32 to be turned on or off. In some embodiments, the capacitive touch sensing chip 46 may take any one of a mechanical sensor, an optical sensor, an ultrasonic sensor, an infrared sensor, and so on to sense the change. In this way, based on the above capacitive touch sensing chip 46, the user's experience may be improved, and an intelligence level of the portable hair removing device 10 may be improved.

Figure 5:
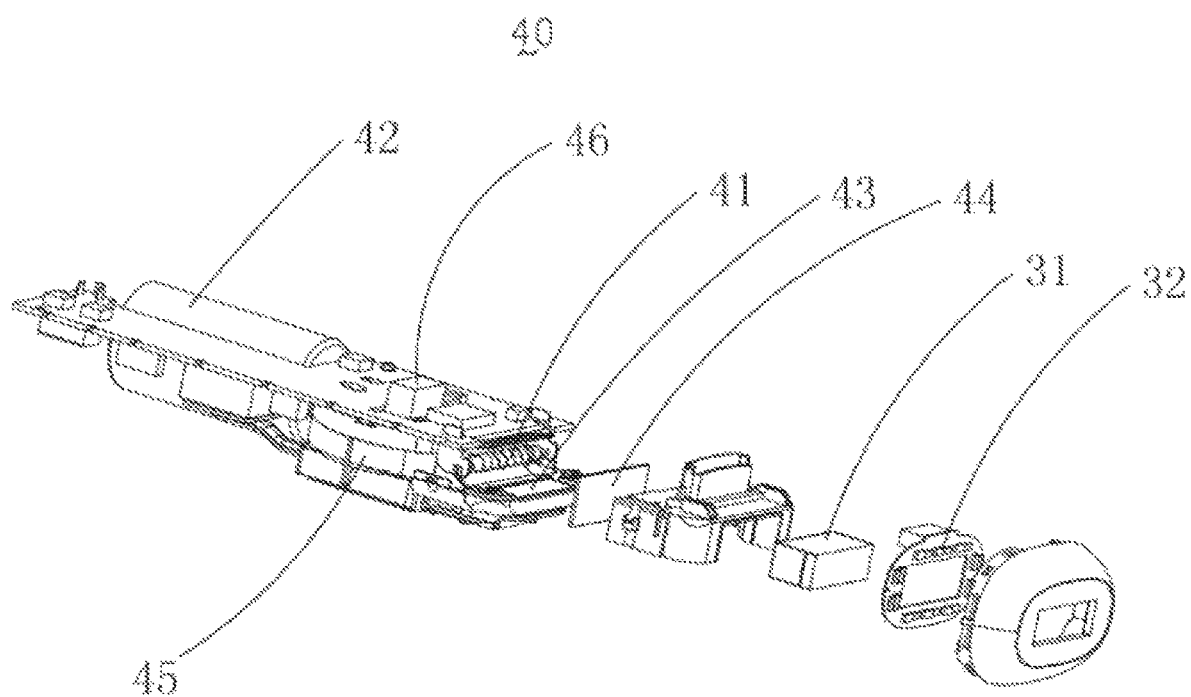
FIG. 5 is a perspective view of a connection portion of the portable hair removing device according to the first embodiment of the present disclosure.

As shown in FIG. 4 and FIG. 5, the portable hair removing device 10 may further include a connection portion 40 received in the shell 20. The connection portion 40 may be connected to the end of the cold-compressing portion 31 away from the fixing portion 35. The emitter 41 may be arranged on an end of the connecting portion 40 near the cold-compressing portion 31. The light emitted from the emitter 41 may contact the skin through the cold-compressing portion 31.

Further, the emitter 41 may be an intense pulsed light (IPL) lamp, disposed on a side of the cold-compressing portion 31 away from another side that contacts the skin. The light emitted by the emitter 41 may reach the user's skin through the cold-compressing portion 31. The color of the emitted light may not be limited. The emitted light may be colored light, composite light, and so on. A wavelength and a frequency of the emitted light may be determined based on the usage.

The connection portion 40 may be various assemblies, such as a power supply assembly 42, a cooling assembly 43, a filter 44, a heat dissipation assembly 45, and so on. The power supply assembly 42 may provide power for the portable hair removing device 10. The cooling assembly 43 may be connected to the cold-compressing portion 31 to cool the cold-compressing portion 31. The filter 44 may be disposed between the cold-compressing portion and the emitter 41 to avoid heat of the emitter 41 from transferring to the cold-compressing portion 31. The heat dissipation assembly 45 may be a heat dissipating fan or a heat dissipating body. Heat may be dissipated to an outside of the portable hair removing device 10 through the heat dissipating fan or the heat dissipating body. The heat dissipation assembly 45 may quickly reduce a temperature of the portable hair removing device 10, such that the user may not feel the burning pain caused by irradiation of the light emitted by the emitter 41. The light emitted by the emitter 41 may pass through the filter 44, such that unwanted wavelengths in the light may be filtered out, achieving better hair removing effects. In addition, the filter 44 may have a better heat insulation effect.

Figure 6:
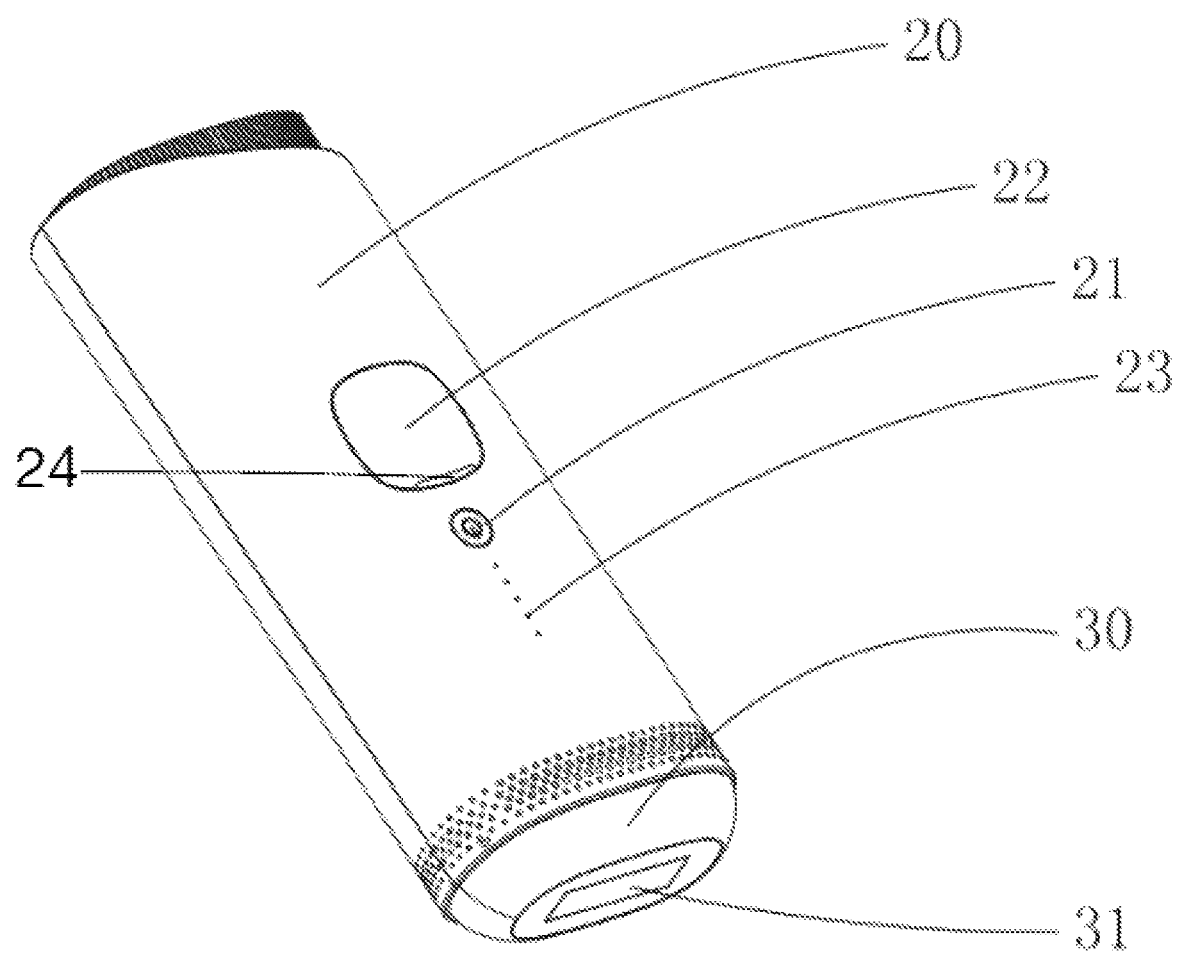
FIG. 6 is another perspective view of the portable hair removing device according to the first embodiment of the present disclosure.

As shown in FIG. 5 and FIG. 6, the shell 20 is further provided with a power switch 21. The power switch 21 may be electrically connected to the head 30, the phototherapeutic lamp 32, the emitter 41, the power supply assembly 42, the cooling assembly 43, the filter 44, and the heat dissipation assembly 45 to control the portable hair removing device 10 to be turned on or off. In detail, the power switch 21 may control the phototherapeutic lamp 32 and the emitter 41 to be turned on or off. In detail, in some embodiments, the power switch 21 may control the wavelength and the frequency of the emitter 41 to control an intensity that the hair removing device 10 removes hair. An intensity of the light of the emitter 41 may be controlled based on the number of times of pressing the power switch 21. That is, a hair removing gear of the portable hair removing device 10 may be adjusted by pressing the power switch 21. The shell 20 may be arranged with a control key 22, and the control key 22 may control the emitter 41 to be turned on or off. A process of operating the portable hair removing device 10 may be as follows. The power switch 21 may be pressed to initiate the portable hair removing device 10. The control key 22 may be pressed to turn on the emitter 41 to emit light. The light may irradiate the skin through the cold-compressing portion 31. The intensity of the light of the emitter 41 may be changed by pressing the power switch 21 for various different times. When the portable hair removing device 10 is approaching the skin to a certain distance, the capacitive touch sensor chip 46 may sense the skin, and the phototherapeutic lamp 32 may be initiated for skin care. When the portable hair removing device 10 is leaving away from the skin to a certain distance, the capacitive touch sensor chip 46 may turn off the phototherapeutic lamp 32.

In some embodiments, the phototherapeutic lamp 32 may be controlled to be turned on or off by the control key 22. The emitter 41 and the phototherapeutic lamp 32 may be controlled to be turned on or off based on the number of times of pressing the control key. In some embodiments, two control keys may be arranged to respectively control the emitter 41 to be turned on or off and control the phototherapeutic lamp 32 to be turned on or off.

The shell 20 may be arranged with at least one display lamp 23. The display lamp 23 may be electrically connected to the control key 22 or the power switch 21. The display lamp 23 being on or off may indicate a working state of the portable hair removing device 10. In detail, in some embodiments, the number of display lamps 23 may be 5. The plurality of display lamps 23 may be configured to indicate a state of power or a working intensity of hair removing and skin care, such that the user may intuitively know the working state of the portable hair removing device 10.

Further as shown in FIG. 5 and FIG. 6, the shell 20 may further be arranged with a skin sensor lamp 24 electrically connected to the capacitive touch sensor chip 46. When the portable hair removing device 10 contacts the skin, the capacitive touch sensor chip 46 on the shell 20 may sense the change in the capacitance value between the wire on the PCB board 33 and the skin. The capacitive touch sensor chip 46 may control the skin sensor lamp 24 to be turned on or off. The skin sensor light 24 may be turned on to inform the user that the portable hair removing device 10 may be used safely. The user may intuitively understand the working state of the portable hair removing device 10 based on the skin sensor light 24 being turned on or off. When the phototherapeutic lamp 32 is on simultaneously, the user may use the portable hair removing device 10 to remove hair and achieve skin care. Further, time may be saved for the user to perform hair removing and skin care.

Figure 7:
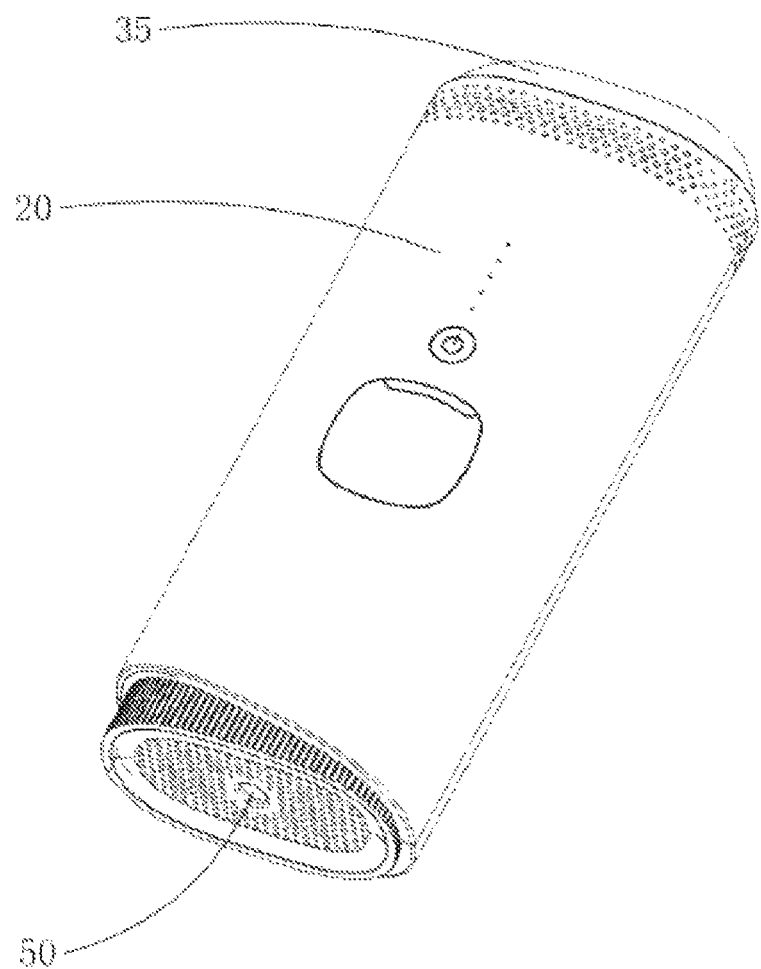
FIG. 7 is still another perspective view of the portable hair removing device according to the first embodiment of the present disclosure.

As shown in FIG. 7, an end of the shell 20 away from the fixing portion 35 may be arranged with a charging port 50. The charging port 50 may be electrically connected to the power supply assembly (not shown) to provide power for the portable hair removing device 10. The charging port 50 may be any one of a DC charging interface, a type-c interface, a micro-usb interface. The portable hair removing device may be charged rapidly through the DC charging interface, improving an operating efficiency of the portable hair removing device. Various charging interfaces may meet various demands of the user.

Figure 8:
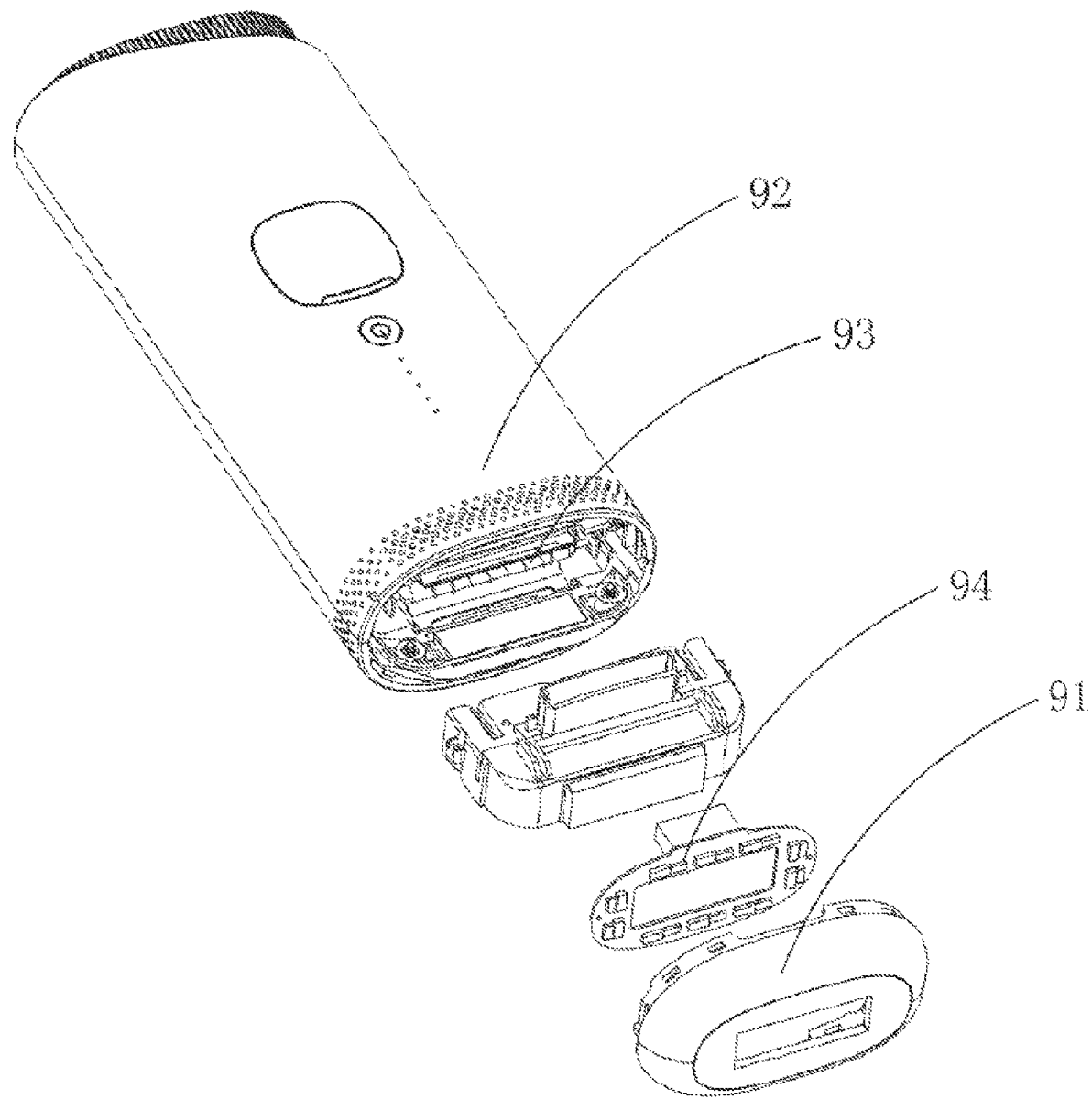
FIG. 8 is an explosive view of a portable hair removing device according to a second embodiment of the present disclosure.

As shown in FIG. 8, a second embodiment of the present disclosure provides a portable hair removing device 90, and the portable hair removing device 90 may be any one of a pulsed light hair removing device (HPL), an E-light hair removing device.

The portable hair removing device 90 includes a head 91, a shell 92 connected to an end of the head 91. An emitter 93 may be arranged in the shell 92 and may emit light. The light emitted from the emitter 93 may act on the skin after passing through the head 91 to remove hair. At least one phototherapeutic lamp 94 may be arranged on the head 91. Light emitted from the phototherapeutic lamp 94 may act on the skin through the head 91 for skin care. The light emitted from the emitter 93 may be any of colored light, e-light and so on.

According to the present disclosure, a hair removing assembly is provided and includes: a head, configured to contact skin of a user and comprising a cold-compressing portion, a fixing portion, and a plurality of phototherapeutic lamps; and a connection portion, connected to the head and extending away from the skin of the user, wherein the connection portion comprises an emitter. A part of the cold-compressing portion extends through and is exposed from an end of the fixing portion away from the connection portion, and the plurality of phototherapeutic lamps are arranged to surround a periphery of the cold-compressing portion. The emitter is configured to emit light that is capable of passing through the cold-compressing portion to irradiate the skin, and each of the plurality of phototherapeutic lamps is configured emit light that is capable of irradiating the skin through the head.

In some embodiments, the phototherapeutic lamps are configured to emit one or a combination of a red light, a blue light, and a yellow light, and a wavelength of the blue light is in a range of 450 nm to 490 nm, and a wavelength of the yellow light is in a range of 567 nm to 607 nm, and a wavelength of the red light is in a range of 620 nm to 660 nm.

In some embodiments, adjacent lamps of the plurality of phototherapeutic lamps are configured to emit lights in different wavelength ranges.

In some embodiments, the head further includes a PCB board arranged between the fixing portion and the cold-compressing portion; a through hole is defined at a position of the PCB board corresponding to the cold-compressing portion; the plurality of phototherapeutic lamps are arranged into a ring shape and arranged to surround the outer periphery of the through hole; and the cold-compressing portion extends through the PCB board and the fixing portion successively.

In some embodiments, a capacitive touch sensor chip is arranged on the connection portion; a wire, which is electrically connected to the capacitive touch sensor chip, is arranged on the PCB board; and the capacitive touch sensor chip is configured to sense a change in a capacitance value between the wire and the skin to control the phototherapeutic lamps to be turned on or turned off.

According to still another aspect of the present disclosure, a portable hair removing device is provided an includes: a shell; a head, connected to the shell and configured to contact skin of a user, wherein the head and the shell cooperatively defines a receiving space, and the head comprises a cold-compressing portion, a fixing portion, and a plurality of phototherapeutic lamps; and a connection portion, received in the receiving space and connected to the head, wherein the connection portion comprises an emitter. A part of the cold-compressing portion is received in the receiving space and another part of the cold-compressing portion extends through and is exposed from an end of the fixing portion away from the connection portion, and the plurality of phototherapeutic lamps are arranged to surround a periphery of the cold-compressing portion. The emitter is configured to emit light that is capable of passing through the cold-compressing portion to irradiate the skin, and each of the plurality of phototherapeutic lamps is configured emit light that is capable of irradiating the skin through the head.

In some embodiments, the shell is arranged with a power switch and a control key; the power switch is electrically connected to the plurality of phototherapeutic lamps and the emitter to control the phototherapeutic lamps and the emitter to be turned on or turned off; and the control key is configured to control a wavelength and a frequency of the emitter and/or to control the phototherapeutic lamps to be turned on or turned off.

In some embodiments, the shell is arranged with at least one display lamp; the display lamp is electrically connected to the control key and/or the power switch, and is configured to indicate a working state of the portable hair removing device by being turned on or turned off.

In some embodiments, a capacitive touch sensor chip is received in the receiving space; the head further comprises a PCB board arranged between the fixing portion and the cold-compressing portion; a wire, which is electrically connected to the capacitive touch sensor chip, is arranged on the PCB board; and the capacitive touch sensor chip is configured to sense a change in a capacitance value between the wire and the skin to control the phototherapeutic lamp to be turned on or turned off.

In some embodiments, the shell is arranged with a skin sensor lamp electrically connected to the capacitive touch sensor chip; and the capacitive touch sensor is configured to control the skin sensor lamp to be turned on or turned off in response to the capacitive touch sensor chip detecting the change in the capacitance value between the wire and the skin.

According to the present disclosure, the portable hair removing device may achieve following technical effects.

1. The portable hair removing device may include a head, a shell connected to an end of the head. An emitter may be arranged in the shell and may emit light. The light emitted by the emitter may pass through the head and act on the skin to remove hair. At least one phototherapeutic lamp may be arranged on the head. Light emitted by the phototherapeutic lamp may act on the skin through the head and perform caring on the skin. Arranging the phototherapeutic lamp on the portable hair removing device enables skin care and hair removing to be achieved at the same time. The portable hair removing device may achieve multiple functions. The phototherapeutic lamp may repair damage of the skin, which is caused while hair is being removed by the emitter.

2. Red light may improve activity of skin cells and promote metabolism of the skin cells. Further, the red light may reduce fine wrinkles, preventing skin from sagging and removing wrinkles. Blue light may cause death of bacteria on the skin, inhibiting growth of the bacteria. Further, the blue light may improve sebum, having anti-inflammatory functions, reducing *acnes*, and reducing pores. Yellow light may brighten the skin and remove spots, providing better skin care effects.

3. Phototherapeutic lamps in different colors, such as red, blue and yellow, may be alternately disposed to improve skin care effects of the skin.

4. The cold-compressing portion may be exposed from the fixing portion to contact the skin, such that the user may be cooled by the cold-compressing portion while using the portable hair removing device to remove hair. In this way, high extent of pain on the skin caused by heat of the light may be reduced, and the cold-compressing portion may not cause damage to the skin.

5. The cold-compressing portion may be arranged on a center of the PCB board. The phototherapeutic lamps are arranged to form a ring shape and disposed to surround a periphery of the cold-compressing portion. The cold-compressing portion and the phototherapeutic lamps are arranged on a same side, facilitating the user to perform hair removing and skin care operations. Arranging the phototherapeutic lamps to surround the periphery of the cold-compressing portion allows a middle area to remove hair and a peripheral area to achieve skin care. In this way, an operational area of the skin that can be treated by the portable hair removing device may be increased.

6. A capacitive touch sensor chip electrically connected to the phototherapeutic lamp may be arranged in the shell. A wire electrically connected to the capacitive touch sensor chip may be arranged on the PCB board. The capacitive touch sensor chip senses a change in a capacitance value between the wire and the skin to control the phototherapeutic lamp to be turned on or turned off, improving the user's experience and an intelligence level of the portable hair removing device. Alternatively, the capacitive touch sensor chip may control the phototherapeutic lamp to be turned on or turned off through a control key, such that the phototherapeutic lamp may be controlled based on the user's demand.

7. The cold-compressing portion may be sapphire. The sapphire may be highly thermal conductive. A light transmission rate that the light passes through the sapphire cold-compressing portion may be maintained while a temperature of the light emitted by the emitter of the portable hair removing device may be reduced.

8. The phototherapeutic lamp may be an LED. The LED may transfer light energy into intracellular energy, accelerating a cell cycle and stimulating fibroblasts to produce collagen. In addition, the LED lamp may not cause any harm and discomfort to the skin.

9. The control key may be arranged on the shell. The control key may control a working state of the emitter. The control key may control specific wavelengths and a frequency of the emitter to further control an intensity of the portable hair removing device, adapting to various skin types or various operating environments.

10. The shell is arranged with at least one display lamp. The display lamp may be electrically connected to the control key or a power switch. The display lamp may be turned on or turned off to indicate the working state of the portable hair removing device. A plurality of display lamps may be arranged to indicate a state of power or an intensity of hair removing and skin care, such that the user may intuitively know an operating state of the portable hair removing device. When the skin contacts the portable hair removing device, the capacitive value between the wire and the skin may change, and the capacitive touch sensor chip on the PCB board may control an induction lamp to be turned on. While the induction lamp is on, the phototherapeutic lamp may be turned on for skin care, and the user may control the light of the hair removing device to operate.

11. The shell may further be arranged with a skin sensor lamp. When the skin contacts the portable hair removing device, the capacitive touch sensor chip on the shell senses the change in the capacitance value between the wire on the PCB board and the skin, the skin sensor lamp may be turned on, indicating that the user may safely use the portable hair removing device. When the phototherapeutic lamp is also turned on at this time point, the user may use the portable hair removing device to achieve hair removing and skin care at the same time. In this way, time may be saved for the user to perform hair removing and skin care.

12. Arranging the phototherapeutic lamps on the portable hair removing device may be applied to a variety of hair removing technology fields. The technical solution may be applied to a wide range of applications, which is highly practical.

What is claimed is:

1. A portable hair removing device, comprising:
    a head;
    a shell, connected to an end of the head; and
    an emitter, capable of emitting light and arranged inside the shell, wherein
    the light emitted from the emitter is configured to pass through the head to act on skin to remove hair;
    a printed circuit board (PCB) is arranged inside the head, the head is arranged with at least one phototherapeutic lamp, the PCB defines a through hole; the at least one phototherapeutic lamp is arranged on the PCB and surround an outer periphery of the through hole; and
    light emitted from the at least one phototherapeutic lamp is configured to act on the skin through the head to provide cares for the skin.

2. The portable hair removing device of claim 1, wherein the phototherapeutic lamp is configured to emit one or a combination of a red light, a blue light, and a yellow light, and a wavelength of the blue light is in a range of 450 nm to 490 nm, and a wavelength of the yellow light is in a range of 567 nm to 607 nm, and a wavelength of the red light is in a range of 620 nm to 660 nm.

3. The portable hair removing device according to claim 2, wherein the number of the at least one phototherapeutic lamp is more than one, and adjacent lamps of the more than one phototherapeutic lamps are configured to emit lights in different wavelength ranges.

4. The portable hair removing device according to claim 1, wherein, the head comprises a cold-compressing portion and a fixing portion;
    an end of the fixing portion away from the shell is configured to contact the skin;
    a part of the cold-compressing portion is received inside the shell and the fixing portion;
    the cold-compressing portion extends through and is exposed from the end of the fixing portion away from the shell;
    the phototherapeutic lamp is arranged to surround an outer periphery of the cold-compressing portion; and
    the light emitted from the emitter is capable of passing through the cold-compressing portion to irradiate the skin.

5. The portable hair removing device according to claim 4, wherein,
    the head further comprises a PCB board arranged between the fixing portion and the cold-compressing portion;
    the through hole of the PCB board corresponding to the cold-compressing portion;
    the number of the at least one phototherapeutic lamp is more than one, and the more than one, and the more than one phototherapeutic lamps are arranged into a ring shape and arranged to surround the outer periphery of the through hole, and the cold-compressing portion extends through the PCB board and the fixing portion sequentially.

6. The portable hair removing device according to claim 5, wherein,
    a capacitive touch sensor chip is arranged inside the shell;
    a wire, which is electrically connected to the capacitive touch sensor chip, is arranged on the PCB board; and the capacitive touch sensor chip is configured to sense a change in a capacitance value between the wire and the skin to control the phototherapeutic lamp to be turned on or turned off.

7. The portable hair removing device according to claim 6, wherein,
the shell is further arranged with a power switch and a control key;
the power switch is electrically connected to the phototherapeutic lamp and the emitter to control the phototherapeutic lamp and the emitter to be turned on or turned off; and
the control key is configured to control a wavelength and a frequency of the emitter and/or to control the phototherapeutic lamp to be turned on or turned off.

8. The portable hair removing device according to claim 7, wherein,
at least one display lamp is arranged on the shell;
the display lamp is electrically connected to the control key and/or the power switch, and is configured to indicate a working state of the portable hair removing device by being turned on or turned off;
the shell is arranged with a skin sensor lamp electrically connected to the capacitive touch sensor chip; and
the capacitive touch sensor is configured to control the skin sensor lamp to be turned on or turned off in response to the capacitive touch sensor chip detecting the change in the capacitance value between the wire and the skin.

9. The portable hair removing device of claim 4, wherein, the cold-compressing portion is made of sapphire, and each of the at least one phototherapeutic lamp is an LED.

10. The portable hair removing device according to claim 1, wherein the portable hair removing device is any one of a pulse light hair removing device and an E-light hair removing device.

11. A hair removing assembly, comprising:
a head, configured to contact skin of a user and comprising a printed circuit board (PCB), a cold-compressing portion, a fixing portion, and a plurality of phototherapeutic lamps; and
a connection portion, connected to the head and extending away from the skin of the user, wherein the connection portion comprises an emitter;
wherein a part of the cold-compressing portion extends through and is exposed from an end of the fixing portion away from the connection portion, and the plurality of phototherapeutic lamps are arranged to surround a periphery of the cold-compressing portion;
the PCB is disposed between the fixing portion and the cold-compressing portion and defines a through hole, the plurality of phototherapeutic lamps are arranged on a side of the PCB facing the fixing portion and surround an outer periphery of the through hole; and
the emitter is configured to emit light that is capable of passing through the cold-compressing portion to irradiate the skin, and each of the plurality of phototherapeutic lamps is configured emit light that is capable of irradiating the skin through the head.

12. The hair removing assembly according to claim 11, wherein the phototherapeutic lamps are configured to emit one or a combination of a red light, a blue light, and a yellow light, and a wavelength of the blue light is in a range of 450 nm to 490 nm, and a wavelength of the yellow light is in a range of 567 nm to 607 nm, and a wavelength of the red light is in a range of 620 nm to 660 nm.

13. The hair removing assembly according to claim 12, wherein adjacent lamps of the plurality of phototherapeutic lamps are configured to emit lights in different wavelength ranges.

14. The hair removing assembly according to claim 11, wherein,
the head further comprises a PCB board arranged between the fixing portion and the cold-compressing portion;
the through hole is defined at a position of the PCB board corresponding to the cold-compressing portion;
the plurality of phototherapeutic lamps are arranged into a ring shape and arranged to surround the outer periphery of the through hole; and
the cold-compressing portion extends through the PCB board and the fixing portion successively.

15. The hair removing assembly according to claim 14, wherein,
a capacitive touch sensor chip is arranged on the connection portion;
a wire, which is electrically connected to the capacitive touch sensor chip, is arranged on the PCB board; and
the capacitive touch sensor chip is configured to sense a change in a capacitance value between the wire and the skin to control the phototherapeutic lamps to be turned on or turned off.

16. A portable hair removing device, comprising:
a shell;
a head, connected to the shell and configured to contact skin of a user, wherein the head and the shell cooperatively defines a receiving space, and the head comprises a printed circuit board (PCB), a cold-compressing portion, a fixing portion, and a plurality of phototherapeutic lamps; and
a connection portion, received in the receiving space and connected to the head, wherein the connection portion comprises an emitter;
wherein a part of the cold-compressing portion is received in the receiving space and another part of the cold-compressing portion extends through and is exposed from an end of the fixing portion away from the connection portion, and the plurality of phototherapeutic lamps are arranged to surround a periphery of the cold-compressing portion;
the PCB is disposed between the fixing portion and the cold-compressing portion and defines a through hole, the part of the cold-compressing portion extends through the through hole of the PCB, and the plurality of phototherapeutic lamps are arranged on a side of the PCB facing the fixing portion; and
the emitter is configured to emit light that is capable of passing through the cold-compressing portion to irradiate the skin, and each of the plurality of phototherapeutic lamps is configured emit light that is capable of irradiating the skin through the head.

17. The portable hair removing device according to claim 16, wherein,
the shell is arranged with a power switch and a control key;
the power switch is electrically connected to the plurality of phototherapeutic lamps and the emitter to control the phototherapeutic lamps and the emitter to be turned on or turned off; and
the control key is configured to control a wavelength and a frequency of the emitter and/or to control the phototherapeutic lamps to be turned on or turned off.

18. The portable hair removing device according to claim 17, wherein,
the shell is arranged with at least one display lamp
the display lamp is electrically connected to the control key and/or the power switch, and is configured to indicate a working state of the portable hair removing device by being turned on or turned off.

19. The portable hair removing device according to claim 16, wherein,
a capacitive touch sensor chip is received in the receiving space;
the head further comprises a PCB board arranged between the fixing portion and the cold-compressing portion;
a wire, which is electrically connected to the capacitive touch sensor chip, is arranged on the PCB board; and
the capacitive touch sensor chip is configured to sense a change in a capacitance value between the wire and the skin to control the phototherapeutic lamp to be turned on or turned off.

20. The portable hair removing device according to claim 19, wherein,
the shell is arranged with a skin sensor lamp electrically connected to the capacitive touch sensor chip; and
the capacitive touch sensor is configured to control the skin sensor lamp to be turned on or turned off in response to the capacitive touch sensor chip detecting the change in the capacitance value between the wire and the skin.

* * * * *